United States Patent [19]

Stähle et al.

[11] 4,213,995
[45] Jul. 22, 1980

[54] 2-PHENYLIMINO-IMIDAZOLIDINES AND SALTS THEREOF

[75] Inventors: Helmut Stähle; Herbert Köppe; Werner Kummer, all of Ingelheim am Rhein; Wolfgang Hoefke, Budenheim, all of Fed. Rep. of Germany; Ludwig Pichler, Vienna, Austria

[73] Assignee: Boehringer Ingelheim GmbH, Ingelheim am Rhein, Fed. Rep. of Germany

[21] Appl. No.: 11,074

[22] Filed: Feb. 12, 1979

[30] Foreign Application Priority Data

Feb. 17, 1978 [DE] Fed. Rep. of Germany ....... 2806811

[51] Int. Cl.$^2$ .................. A61K 31/415; C07D 233/50
[52] U.S. Cl. .................. 424/273 R; 548/315
[58] Field of Search .................. 548/315; 424/273 R

[56] References Cited

U.S. PATENT DOCUMENTS

| 3,236,857 | 2/1966 | Zeile et al. | 548/315 |
| 3,468,887 | 9/1969 | Stähle et al. | 548/315 |
| 3,595,961 | 7/1971 | Stähle et al. | 548/315 |
| 4,025,607 | 5/1977 | Stähle et al. | 548/315 |

FOREIGN PATENT DOCUMENTS

| 623305 | 10/1962 | Belgium | 548/315 |
| 653933 | 10/1964 | Belgium | 548/315 |
| 687656 | 9/1966 | Belgium | 548/315 |
| 687657 | 9/1966 | Belgium | 548/315 |
| 705944 | 10/1967 | Belgium | 548/315 |
| 2356005 | 5/1975 | Fed. Rep. of Germany | 548/315 |
| 1506408 | 11/1967 | France | 548/315 |

*Primary Examiner*—Natalie Trousof
*Attorney, Agent, or Firm*—Hammond & Littell, Weissenberger & Muserlian

[57] ABSTRACT

Compounds of the formula

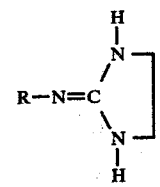

wherein R is 2,6-dichloro-4-hydroxymethyl-phenyl; 2-chloro-4-methyl-5-amino-phenyl; 2,5-dichloro-4-methyl-phenyl; 2-chloro-4-methyl-5-nitro-phenyl; 2,3-dichloro-4-methyl-phenyl; 2-chloro-4-methyl-6-nitro-phenyl; 2-chloro-4-methyl-6-amino-phenyl; 2,4,6-trifluorophenyl; tetrafluoro-phenyl; or 3-bromo-4-fluoro-phenyl; and non-toxic, pharmacologically acceptable acid addition salts thereof. The compounds as well as their salts are useful as hypotensives.

3 Claims, No Drawings

2-PHENYLIMINO-IMIDAZOLIDINES AND SALTS THEREOF

This invention relates to novel 2-phenyliminoimidazolidines and acid addition salts thereof, as well as to methods of preparing these compounds, pharmaceutical compositions containing them as active ingredients, and methods of using them as hypotensives.

THE PRIOR ART

Because of their outstanding pharmacological and therapeutic properties, 2-phenylimino-imidazolidines have for a long time commanded strong interest in the pharmaceutical industry. Therefore, compounds of this type have often been reported in the literature and are disclosed, for example, in Belgian Pat. Nos. 623,305; 653,933; 687,656; 687,657; and 705,944. These prior disclosures also describe the principal methods for the preparation of 2-phenyliminoimidazolidines.

DESCRIPTION OF THE INVENTION

More particularly, the present invention relates to a novel group of 2-(substituted phenyl-imino)-imidazolidines represented by the formula

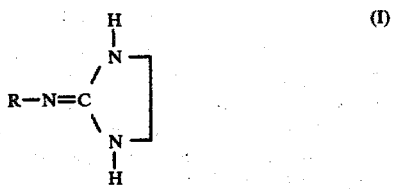

wherein R is 2,6-dichloro-4-hydroxymethyl-phenyl; 2-chloro-4-methyl-5-amino-phenyl; 2,5-dichloro-4-methyl-phenyl; 2-chloro-4-methyl-5-nitro-phenyl; 2,3-dichloro-4-methyl-phenyl; 2-chloro-4-methyl-6-nitro-phenyl; 2-chloro-4-methyl-6-amino-phenyl; 2,4,6-trifluorophenyl; tetrafluoro-phenyl; or 3-bromo-4-fluorophenyl; and non-toxic, pharmacologically acceptable acid addition salts thereof.

The compounds embraced by formula I may be prepared by the following methods:

Method A

By reacting a compound of the formula

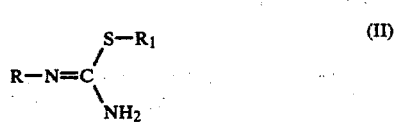

wherein
R has the same meanings as in formula I, and
$R_1$ is hydrogen, or alkyl of 1 to 4 carbon atoms, or an acid addition salt thereof, with ethylenediamine or an acid addition salt thereof.

The reaction is performed at temperatures between 0° and 200° C., with or without a solvent. Polar protic, polar aprotic or non-polar solvents may be used. If the reaction is performed without a solvent, elevated temperatures should be applied. The reaction time depends upon the reactivity of the reactants and varies between a few minutes and several hours.

Method B

For the preparation of those compounds of the formula I where R is nitro-substituted phenyl, by nitrating 2-(2-chloro-4-methyl-phenylimino)-imidazolidine, and separating the isomeric reaction products.

Method C

For the preparation of those compounds of the formula I where R is amino-substituted phenyl, by reducing the nitro-substituted compounds obtained pursuant to method A or B.

Method D

For the preparation of 2-(2,3-dichloro-4-methyl-phenylimino)-imidazolidine and 2-(2,5-dichloro-4-methylphenylimino)-imidazolidine, by chlorinating 2-(2-chloro-4-methyl-phenylimino)-imidazolidine, and separating the isomeric reaction products. The chlorination may be effected with hydrochloric acid in the presence of an oxidizing agent, such as hydrogen peroxide.

The starting compounds required for methods A, B, and D are disclosed in Belgian Pat. Nos. 623,305, 687,657 and 705,944.

The compounds embraced by formula I above are organic bases and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methanesulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-(2,6-Dichloro-4-hydroxymethyl-phenylimino)-imidazolidine hydrochloride by method A A mixture of 7.85 gm (0.02 mol) of 2-(2,6-dichloro-4-hydroxy-methyl-phenyl)-S-methyl-isothiouronium iodide, 20 ml of n-butanol and 2 ml of ethylenediamine was refluxed for 10 hours. Thereafter, the organic solvent was removed in vacuo, the residue was dissolved in methanol, the solution was purified with activated charcoal and filtered, and the filtrate was admixed with aqueous 50% potassium hydroxide while adding ice. The precipitate formed thereby was collected, dried and taken up in absolute methanol. The resulting solution was made acid to Congo red with ethereal hydrochloric acid, ether was added, and the resulting precipitate was collected and dried. 2.4 gm (40.5% of theory) of the compounds of the formula

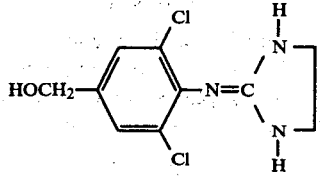

were obtained, it had a melting point of 238° C., and an $R_f$-value of 0.5 in the mobile phase 50 parts benzene, 40 parts dioxane, 5 parts ethanol and 5 parts ammonium hydroxide; carrier: silicagel; detector: potassium iodoplatinate.

The starting compound was obtained by chlorinating p-amino-benzoic acid, reducing the resulting 3,5-dichloro-4-amino-benzoic acid with lithium aluminum hydride, reacting the resulting amine with thiocyanate to form the corresponding thiourea, and methylating the latter with methyl iodide.

EXAMPLE 2

2-(5-Amino-2-chloro-4-methyl-phenylimino)-imidazolidine by method C 25.4 gm (0.10 mol) of 2-(2-chloro-4-methyl-5-nitro-phenylimino)-imidazolidine were hydrogenated in a shaker autoclave at 25° to 30° C. and atmospheric pressure in the presence of Raney nickel and in a 1:1 mixture of methanol and tetrahydrofuran until the theoretical amount of hydrogen had been absorbed. Thereafter, the catalyst was separated by suction filtration, and the filtrate was evaporated to dryness in vacuo. The residue was dissolved in 2 N hydrochloric acid, and the solution was extracted with ether; the ether extracts were discarded. The aqueous phase was fractionally extracted with ether at stepwisely increasing pH-values (alkalization with 2 N NaOH), and the uniform fractions were combined, dried over magnesium sulfate and filtered. The ether was removed from the filtrate in vacuo until the weight of the residue remained constant, leaving 6.85 gm (30.5% of theory) of 2-(5-amino-2-chloro-4-methylphenylimino)-imidazolidine, m.p. 155°–157° C., $R_f$-value 0.70 in the mobile phase 70 parts ethyl acetate, 50 parts isopropanol, 20 parts concentrated ammonium hydroxide; carrier: silicagel G; detector: ultraviolet light and potassium iodoplatinate.

EXAMPLE 3

2-(2,5-Dichloro-4-methyl-phenylimino)-imidazolidine by method D 6.08 gm (0.029 mol) of 2-(2-chloro-4-methyl-phenylimino)-imidazolidine were dissolved in 50 ml of concentrated hydrochloric acid, 200 mgm of ferric chloride were added to the solution, and the mixture was heated to 45° C. while vigorously stirring. 3 ml of 30% hydrogen peroxide were now slowly added dropwise, during which time the temperature of the reaction mixture rose to a maximum of 70° C. As soon as the temperature dropped to 40° C. again, the reaction had gone to completion. The reaction mixture was now admixed with ice, and the aqueous mixture was extracted with ether; the ether extracts were discarded. The aqueous phase was fractionally extracted at stepwisely increasing pH-values (alkalization with 2N NaOH), and the uniform fractions were combined, dried over magnesium sulfate and filtered. The ether was evaporated from the filtrate in vacuo, and the residue was dried, yielding 0.45 gm (6.35% of theory) of 2-(2,5-dichloro-4-methyl-phenylimino)-imidazolidine, m.p. 190°–191° C., $R_f$-value 0.6 in the mobile phase 50 parts benzene, 40 parts dioxane, 5 parts ethanol, 5 parts concentrated ammonium hydroxide; carrier: silicagel G; detector: potassium iodoplatinate.

EXAMPLE 4

2-(2-Chloro-4-methyl-5-nitro-phenylimino)-imidazolidine by method B 6.4 gm (0.0234 mol) of 2-(2-chloro-4-methyl-phenylimino)-imidazolidine nitrate were added slowly over a period of 15 minutes to 10 ml of concentrated sulfuric acid at 20° C., while slightly cooling and vigorously stirring. The viscous reaction mixture was allowed to stand at room temperature for two hours, whereupon ice was added thereto, and the precipitate formed thereby was filtered off, recrystallized from methanol and dried. Yield: 2 gm (33.5% of theory) of 2-(2-chloro-4-methyl-5-nitro-phenylimino)-imidazolidine, m.p. 198°–201° C.; $R_f$-value 0.7 in the mobile phase 50 parts benzene, 40 parts dioxane, 5 parts ethanol and 5 parts ammonium hydroxide; carrier: silicagel G; visualization: ultraviolet light and potassium iodoplatinate.

EXAMPLE 5

2-(2,3-Dichloro-4-methyl-phenylimino)-imidazolidine by method D 60.8 gm (0.29 mol) of 2-(2-chloro-4-methyl-phenylimino)-imidazolidine were dissolved in 280 ml of concentrated hydrochloric acid, the solution was heated to 45° C., and 35.5 ml of 30% hydrogen peroxide were added dropwise over a period of 30 minutes, while vigorously stirring; the temperature of the reaction mixture rose to a maximum of 60° C. during that time. The reaction mixture was allowed to stand at 60° C. for one hour. The thin-layer chromatogram of a sample showed that the reaction mixture contained four different reaction products besides some unreacted starting material. The isolation and separation of these reaction products by repeated fractional extraction with ether at stepwisely increasing pH-values (alkalization with 2 N NaOH) and purification by column chromatography yielded, inter alia, 0.40 gm (0.6% of theory) of 2-(2,3-dichloro-4-methyl-phenylimino)-imidazolidine, m.p. 158°–162° C., $R_f$-value 0.1 in the mobile phase 20 parts methanol, 10 parts acetone, 50 parts chloroform; carrier: silicagel, visualization: ultraviolet light and potassium iodoplatinate.

EXAMPLE 6

2-(2-Chloro-4-methyl-6-nitro-phenylimino)-imidazolidine by method B 50 gm (0.183 mol) of 2-(2-chloro-4-methyl-phenylimino)-imidazolidine nitrate were slowly added over a period of two hours to 70 ml of concentrated sulfuric acid at 5°–10° C., while slightly cooling with ice and thoroughly stirring and the resulting black solution was stirred for one hour more at 5° C. Thereafter, ice was added, the aqueous mixture was made alkaline with 5 N sodium hydroxide, and the precipitate formed thereby was collected, recrystallized from methanol and separated from the mother liquor by suction filtration. The methanol was distilled out of the filtrate, and the residue was eluted on a silicagel column (mobile phase: 20 parts methanol, 10 parts acetone, 50 parts chloroform). The thin-layer chromatographically uniform fractions were combined and evaporated in vacuo, and the solid residue was dried, yielding 0.4 gm (0.86% of theory) of 2-(2-chloro-4-methyl-6-nitrophenylimino)-imidazolidine, m.p. 198° C., $R_f$-value 0.7 in the mobile phase 50 parts benzene, 40 parts dioxane, 5 parts ethanol and 5 parts concentrated ammonium hydroxide; carrier: silicagel G, visualization: ultraviolet light and potassium iodoplatinate.

EXAMPLE 7

2-(2-Amino-6-chloro-4-methyl-phenylimino)-imidazolidine by method C 3.05 gm (0.012 mol) of 2-(2-chloro-4-methyl-6-nitrophenylimino)-imidazolidine were hydrogenated in a shaker autoclave at 25°-30° C. and atmospheric pressure in the presence of Raney nickel and in a 1:1 mixture of methanol and tetrahydrofurn until the theoretical amount of hydrogen had been absorbed. Thereafter, the catalyst was separated by suction filtration, and the filtrate was evaporated in vacuo until the weight of the residue remained constant. Yield: 2.6 gm (96.5% of theory) of 2-(2-amino-6-chloro-4-methyl-phenylimino)-imidazolidine, an oily substance having an $R_f$-value of 0.3 in the mobile phase 50 parts benzene, 40 parts dioxane, 5 parts ethanol and 5 parts concentrated ammonium hydroxide; carrier: silicagel G; visualization: ultraviolet light and potassium iodoplatinate.

EXAMPLE 8

2-(2,4,6-Trifluoro-phenylimino)-imidazolidine hydrochloride by method A

A mixture of 17.4 gm (0.05 mol) of N-(2,4,6-trifluorophenyl)-S-methyl-isothiouronium iodide, 5 ml of ethylenediamine (150% of the stoichiometrically required amount) and 80 ml of n-butanol was refluxed for five hours. Thereafter, the solvent was evaporated in vacuo, the residue was dissolved in a mixture of 2 N hydrochloric acid and water, and the solution was extracted with ether; the ether extracts were discarded. The aqueous phase was made alkaline with 2 N sodium hydroxide, and the precipitate formed thereby was collected and dried, yielding 2-(2,4,6-trifluorophenylimino)-imidazolidine base, m.p. 148°-150° C.

The base was dissolved in a little methanol, the resulting solution was filtered, and the filtrate was made acid to Congo red with ethereal hydrochloric acid. Ether was then added to the acidic solution, whereupon a white substance crystallized out which was collected by suction filtration, washed with ether and dried.

Yield: 4.55 gm (36.16% of theory) of the hydrochloride, m.p. 260°-261° C., $R_f$-value 0.6 in the mobile phase 50 parts benzene, 40 parts dioxane, 5 parts concentrated ammonia and 5 parts ethanol; carrier: silicagel G with fluoroescent pigment ZS; visualization: ultraviolet light and potassium iodoplatinate.

EXAMPLE 9

2,(2,3,4,6-Tetrafluoro-phenylimino)-imidazolidine hydrochloride by method A

A mixture of 10.32 gm (0.028 mol) of N-(2,3,4,6-tetrafluoro-phenyl)-S-methyl-isothiouronium iodide, 2.8 ml of ethylene diamine (150% of the stoichiometrically required amount) and 45 ml of n-butanol was refluxed for 5 hours. Thereafter, the solvent was evaporated in vacuo, the residue was dissolved in a mixture of 2 N hydrochloric acid and water, and the solution was extracted with ether; the ether extracts were discarded. The aqueous phase was made alkaline with 2 N sodium hydroxide, and the solid precipitate formed thereby was collected and dried, yielding 2-(2,3,4,6-tetrafluorophenylimino)-imidazolidine base, m.p. 167°-168° C.

The base was dissolved in a little methanol, the solution was filtered, and the filtrate was made acid to Congo red with ethereal hydrochloric acid. Ether was added to the acidic solution, whereupon a white substance crystallized out, which was collected by vacuum filtration, washed with ether and dried. Yield: 3.7 gm (48.67% of theory) of the hydrochloride, m.p. 236°-237° C.; $R_f$-value 0.7 in the mobile phase 50 parts benzene, 40 parts dioxane, 5 parts concentrated ammonia and 5 parts ethanol. Carrier: silicagel G with fluorescent pigment ZS; visualization: ultraviolet light and potassium iodoplatinate.

EXAMPLE 10

2-(2,3,5,6-Tetrafluoro-phenylimino)-imidazolidine hydrochloride by method A

A mixture of 14.64 gm (0.04 mol) of N-(2,3,5,6-tetrafluoro-phenyl)-S-methyl-isothiouronium iodide, 4 ml of ethylenediamine (150% of the stoichiometrically required amount) and 64 ml of n-butanol was refluxed for 5 hours while stirring. Thereafter, the solvent was evaporated in vacuo, the residue was dissolved in a mixture of 2 N hydrochloric acid and water, and the solution was extracted with ether; the ether extracts were discarded. The aqueous phase was made alkaline with 2 N sodium hydroxide, and the solid precipitate formed thereby was collected and dried, yielding 2-(2,3,5,6-tetrafluoro-phenylimino)-imidazolidine base, m.p. 147°-148° C.

The base was dissolved in a little methanol, the solution was filtered, and the filtrate was made acid to Congo red with ethereal hydrochloric acid. Ether was added to the acidic solution, whereupon a white substance crystallized out, while was collected by vacuum filtration, washed with ether and dried. Yield: 6.8 gm (63.05% of theory) of the hydrochloride, m.p. 310°-311° C.; $R_f$-value 0.7 in the mobile phase 50 parts benzene, 40 parts dioxane, 5 parts concentrated ammonia and 5 parts ethanol. Carrier: silicagel G with fluoroescent pigment ZS; visualization: ultraviolet light and potassium iodoplatinate.

EXAMPLE 11

2-(2,3,4,5-Tetrafluoro-phenylimino)-imidazolidine hydrochloride by method A

A mixture of 9.34 gm (0.0255 mol) of N-(2,3,4,5-tetrafluoro-phenyl)-S-methyl-isothiouronium iodide, 2.6 ml of ethylenediamine (150% of the stoichiometrically required amount) and 40 ml of n-butanol was refluxed for 5 hours while stirring. Thereafter, the solvent was evaporated in vacuo, the residue was dissolved in a mixture of 2 N hydrochloric acid and water, and the solution was extracted with ether; the ether extracts were discarded. The aqueous phase was made alkaline with 2 N sodium hydroxide, and the solid precipitate formed thereby was collected and dried, yielding 2-(2,3,4,5-tetrafluoro-phenylimino)imidazolidine base, m.p. 141°-143° C.

The base was dissolved in a little methanol, the solution was filtered, and the filtrate was made acid to Congo red with ethereal hydrochloric acid. Ether was added to the acidic solution, whereupon a white substance crystallized out, which was collected by vacuum filtration, washed with ether and dried. Yield: 3.35 gm (48.73% of theory) of the hydrochloride, m.p. 184°-185° C.; $R_f$-value 0.5 in the mobile phase 50 parts benzene, 40 parts dioxane, 5 parts concentrated ammonia and 5 parts ethanol. Carrier: silicagel G with fluorescent pigment ZS; visualization: ultraviolet light and potassium iodoplatinate.

The compounds of the present invention, that is, those embraces by formula I and their non-toxic, pharmacologically acceptable acid addition salts, have useful pharmacodynamic properties. More particularly, they exhibit hypotensive activity in warm-blooded animals, such as rabbits, and are therefore useful for the treatment of hypertonia.

For pharmaceutical purposes the compounds of the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0008 to 0.05 mgm/kg body weight, preferably 0.0016 to 0.17 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 12

Tablets

The tablet composition is compounded from the following ingredients:

| | |
|---|---|
| 2-(2,6-Dichloro-4-hydroxymethyl-phenylimino)-imidazolidine hydrochloride | 5 parts |
| Lactose | 65 parts |
| Corn starch | 130 parts |
| Sec. Calcium phosphate | 40 parts |
| Soluble starch | 3 parts |
| Magnesium stearate | 3 parts |
| Colloidal silicic acid | 4 parts |
| Total | 250 parts |

Preparation

The active ingredient is admixed with a portion of all of the excipients, the mixture is moistened with an aqueous solution of the soluble starch, the moist mass is granulated by passing it through a screen, and the granulate is dried. The dry granulate is admixed with the remainder of the excipients, and the composition is compressed into 250 mgm/tablets. Each tablet is an oral dosage unit composition containing 5 mgm of the active ingredient.

EXAMPLE 13

Hypodermic solution

The solution is compounded from the following ingredients:

2-(5-Amino-2-chloro-4-methyl-phenylimino)-imidazolidine hydrobromide: 1.0 parts
Sodium chloride: 18.0 parts
Distilled water q.s.ad: 2000.0 parts by vol.

Preparation

The active ingredient and the sodium chloride are dissolved in the distilled water, and the solution is filled under aseptic conditions and in an atmosphere of nitrogen into 2 cc-ampules which are subsequently sterilized and sealed. the contents of each ampule are an injectable dosage unit composition containing 1 mgm of the active ingredient.

EXAMPLE 14

Drop solution

The solution is compounded from the following ingredients:

2-(2,5-Dichloro-4-methyl-phenylimino)-imidazolidine hydrobromide: 0.02 parts
Methyl p-hydroxy-benzoate: 0.07 parts
Propyl p-hydroxy-benzoate: 0.03 parts
Demineralized water q.s.ad: 100.0 parts by vol.

Preparation

The active ingredient and the p-hydroxy-benzoates are dissolved in the demineralized water. 5 ml (20 drops) of the solution are an oral dosage unit composition containing 1 mgm of the active ingredient.

Any one of the other compounds embraced by formula I or a non-toxic, pharmacologically acceptable acid addition salt thereof may be substituted for the particular active ingredient in Examples 12 through 14. Likewise, the amount of active ingredients in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without dparting from the spirit of the invention or the scope of the appended claims.

We claim:

1. A compound of the formula

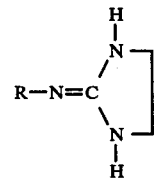

wherein R is 2,6-dichloro-4-hydroxymethyl-phenyl or tetrafluoro-phenyl; or a non-toxic, pharmacologically acceptable acid addition salt thereof.

2. A hypotensive pharmaceutical dosage unit composition consisting essentially of an inert pharmaceutical carrier and an effective hypotensive amount of a compound of claim 1.

3. The method of reducing the blood pressure of a warm-blooded animal in need thereof, which comprises enterally or parenterally administering to said animal an effective hypotensive amount of a compound of claim 1.

* * * * *

UNITED STATES PATENT AND TRADEMARK OFFICE
CERTIFICATE OF CORRECTION

PATENT NO. : 4,213,995
DATED : July 22, 1980
INVENTOR(S) : HELMUT STÄHLE ET AL.

It is certified that error appears in the above-identified patent and that said Letters Patent are hereby corrected as shown below:

Column 6, line 39: "while was collected" should read -- which was collected --.

Column 7, line 4: "184°-185°" should read -- 184°-186° --.

Column 8, line 44: "dparting" should read -- departing --.

Signed and Sealed this

Eleventh Day of November 1980

[SEAL]

Attest:

SIDNEY A. DIAMOND

Attesting Officer

Commissioner of Patents and Trademark